United States Patent [19]

Carniglia

[11] Patent Number: 4,871,718

[45] Date of Patent: Oct. 3, 1989

[54] COMPOSITION OF MATTER FOR INCREASING INTRACELLULAR ATP LEVELS AND PHYSICAL PERFORMANCE LEVELS AND FOR INCREASING THE RATE OF WOUND REPAIR

[75] Inventor: Francis J. Carniglia, Windsor Locks, Conn.

[73] Assignee: Raymond A. Roncari, Windsor Locks, Conn.

[21] Appl. No.: 139,288

[22] Filed: Dec. 29, 1987

[51] Int. Cl.$^4$ .............................................. A61K 31/70
[52] U.S. Cl. ........................................ 514/23; 514/47; 514/48
[58] Field of Search ............... 514/23, 47, 48; 435/87, 435/88

[56] References Cited

U.S. PATENT DOCUMENTS

| | | | |
|---|---|---|---|
| 2,417,841 | 3/1947 | Ruskin | 514/47 |
| 2,844,514 | 7/1958 | Morell et al. | 435/87 |
| 3,009,859 | 11/1961 | Laborit et al. | 514/47 |
| 3,104,203 | 9/1963 | Ruskin et al. | 514/47 |
| 3,157,635 | 11/1964 | Tanaka et al. | 536/28 |
| 3,298,923 | 1/1967 | Banno et al. | 435/88 |
| 3,329,567 | 7/1967 | Ruskin et al. | 514/26 |
| 3,686,392 | 8/1972 | Hamada et al. | 514/47 |
| 3,819,830 | 6/1974 | Yoshimura et al. | 514/47 |
| 3,823,234 | 7/1974 | Mauvernay | 514/47 |
| 3,931,402 | 1/1976 | Ghielmetti et al. | 514/23 |
| 3,978,213 | 8/1976 | Lapinet et al. | 514/47 |
| 4,046,879 | 9/1977 | Swetly | 514/47 |
| 4,078,971 | 3/1978 | Arkles et al. | 435/92 |
| 4,088,756 | 5/1978 | Voorhees | 514/47 |
| 4,207,315 | 6/1980 | Voorhees et al. | 514/47 |
| 4,211,770 | 7/1980 | Voorhees | 514/47 |
| 4,308,257 | 12/1981 | Caspe | 514/47 |
| 4,362,745 | 12/1982 | Johnston | 514/566 |
| 4,363,818 | 12/1982 | Gottlieb | 514/561 |
| 4,414,202 | 11/1983 | Silvetti | 424/147 |
| 4,427,650 | 1/1984 | Stroetmann | 424/46 |
| 4,546,095 | 10/1985 | Markov | 514/23 |
| 4,554,253 | 11/1985 | Imahori et al. | 435/288 |
| 4,575,498 | 3/1986 | Holmes et al. | 514/47 |
| 4,604,286 | 8/1986 | Kawajiri | 514/23 |
| 4,605,644 | 8/1986 | Foker | 514/23 |
| 4,767,785 | 8/1968 | Georgieff | 514/561 |
| 4,772,591 | 9/1988 | Meisner | 514/23 |

Primary Examiner—Ronald W. Griffin
Attorney, Agent, or Firm—McCormick, Paulding & Huber

[57] ABSTRACT

A composition of matter for increasing the intracellular synthesis of ATP. The composition consists of amino acids, metabolites, electrolyte and a pentose sugar. When applied to wounds, the invention increases the rate of wound repair. When administered orally, the invention increases ATP blood levels and physical performance levels.

17 Claims, 8 Drawing Sheets

COMPOSITION OF MATTER FOR INCREASING INTRACELLULAR ATP LEVELS AND PHYSICAL PERFORMANCE LEVELS AND FOR INCREASING THE RATE OF WOUND REPAIR

BACKGROUND OF THE INVENTION

1. Field of the Invention

This invention relates to a composition of matter which provides the components required for increasing the intracellular synthesis of adenosine 5-triphosphate (hereinafter ATP). More particularly, the present invention relates to a composition which increases ATP levels and physical performance levels when administered orally and to a pharmaceutical preparation which increases the rate of wound repair when applied locally.

2. The Role of ATP in Cell Metabolism

The chemistry and biology of the adenine nucleotides began in 1847 with their isolation by Liebig (Liebig's ann 62: 317, 1847). At first these compounds were thought to be only degradation components of the nucleic acids; however, it was later realized that the chemistry and biology of the nucleotides derive from the purine bases adenine and hydroxanthine to which the five-carbon sugar d-ribose is added to form biologically active nucleoside precursors. The addition of phosphate to a nucleoside (purine base+pentose+phosphate) forms a nucleotide. By the early 1940's, attempts were being made to utilize the nucleotide ATP in the form of a Ca or Mg salt for energy enhancement.

ATP plays a diverse role in intermediary cell metabolism due to its high energy phophate bonds. This was first demonstrated by Lipmann with regard to ATP's role in glycolysis (*Advances in Enzy. Mol.* 1, 99, 1947). Within the next four years, the central role ATP plays in respiration, carbohydrate metabolism, fat metabolism and the synthesis of urea and glutamine was clearly established.

Energy for muscular contraction and hence work comes from the hydrolysis of ATP. In skeletal muscle, ATP is hydrolized to adenosine diphosphate (hereinafter ADP) by the enzyme myosin ATPase. The hydrolysis of ATP to ADP is accompanied by the release of energy, and the process may be represented by the following reaction:

Muscular contraction proceeds for a few seconds during this liberation of energy.

ATP blood levels are only reported to decrease over short time periods. For example, ATP blood levels have been observed to drop in humans and horses during periods of highly intensive exercise. It is apparent that if contractile activity is to be maintained during such exercise, rapid synthesis of ATP must occur intracellularly (Hodgson, *Equine Practice,* Vet Clinics, Dec. 1985).

There are two processes which provide intracellular replenishment of ATP: oxidative (aerobic) phosphorylation of substrates from circulating fatty acids and glucose and intramuscular glycogen and triglycerides; and, anaerobic phosphorylation in which ATP is generated from creatine phosphate, circulating glucose and glycogen stores.

In oxidative phosphorylation, muscle cells are unable directly to obtain ATP circulating in the blood; the reason appears to be associated with the binding of ATP's triphosphate component to the cell membrane. In most cells, the fewer the phosphates attached to the nucleotide, the more readily the nucleotide will be absorbed by the cell. Thus, cells will generally absorb adenosine monophosphate (hereinafter AMP) faster than ADP, and they will absorb ADP faster than ATP. AMP or ADP which has been absorbed by the cell must be rephosphorylated intracellularly to form ATP. This process involves the passage of hydrogen molecules from one step to the next along a reaction chain with the concurrent release of large amounts of chemical energy. Approximately half of this energy is utilized by the cell for further rephosphorylation of AMP or ADP, and the balance is given off as heat energy.

At the onset of exercise or under conditions where oxygen transport is insufficient, ATP stores built by oxidative phosphorylation become depleted; ATP, however, must still be made available to provide energy for muscular contraction. Anaerobic phosphorylation mechanisms are utilized by the muscle cells to provide the required ATP under these circumstances. Anaerobic phosphorylation occurs solely in the cell cytosol and mitochondria and involves high energy phosphates (phosgenes) represented by creatine phosphate (hereinafter CP), ADP and AMP.

The most important anaerobic phosphorylation mechanism appears to involve CP and may be represented as follows:

A second mechanism for restoring ATP levels in muscle cells is the myokinase reation. Through this mechanism, muscle cells condense two molecules of ADP to form one molecule of ATP and one molecule of AMP. The mechanism may be represented as follows:

Substrate utilization through oxidative phosphorylation in, for example, exercising humans or athletic animals such as racehorses, depends on the intensity of the work. ATP contributions through oxidative phosphorylation are directly related to the pace and speed of muscular contraction. As exercise continues, ATP becomes depleted and is restored by donations of energy from CP. When CP is depleted, other stores of energy are required. Although the myokinase reaction is present in skeletal muscle, it may have only a limited role in energy metabolism. Glycolysis and its end product pyruvate, which may be converted to lactate, provide the ongoing energy supply. In horses, the glycolytic process reaches peak efficiency approximately thirty seconds from the onset of exercise. Because equines have a large store of glycogen, this substrate is able to provide a considerable source of energy during exercise.

3. The Role of ATP in Wound Repair

The ATP dependency of the contractile mechanism in both striated and smooth muscle cells is signaled by the presence of divalent cations, particularly $Ca++$ and $Mg++$. It is significant that the content and function of calcium and magnesium in isolated myofibroblasts are analogous to their content and function in smooth muscle cells; hence, it appears that the contractile mechanism of the myofibroblasts is also dependent on ATP (*Science,* 1644–48, March 1987).

The myofibrolasts are a specialized population of fibroblasts; fibroblasts are connective tissue cells which, when differentiated, form binding and supporting connective tissue (collagen) such as tendons. The myofibroblasts are atypical fibroblasts which combine some of the ultrastructural features of fibroblasts and smooth muscle cells. The myofibroblasts have a dense collection of microfilament bundles that are rich in actin filaments. These bundles are muscle-like contractile fibrils.

A positive correlation has been established between the rate of wound repair in animals and the number of myofibroblasts present at the wound site. In many instances a wound lacks sufficient vascular development to support the nutritional needs of repair processes. This is so even when additional nutrients are provided by intravenous administration, since the primary means these nutrients have for reaching the repair site is by diffusion from the vascularized regions adjacent to the wound. An inadequate regenerative capacity of the host is particularly acute where the wound surface to be closed by granulation is large. In such instances, contraction of the wound surface, characterized by the movement of intact dermis over the wound site, plays an important role in the repair process by lessening the size of the wound gap (*J. Cenat.,* 89, 114–123, 1955). It is myofibroblasts, with their muscle-like contractile fibrils, which produce such wound contraction.

As noted above, the contractile mechanism of these fibrils is dependent on ATP. Thus, the rate of localized wound contraction produced by the myofibroblasts is dependent on the amount of ATP available to them as an intracellular energy source. Moreover, ATP serves as an energy source for other wound repair processes, including granulation of the wound by fibroblasts, gluconeogenesis and protein synthesis, and epithelialization.

In view of the diverse role ATP plays in cell metabolism and the importance of ATP to overall animal biochemistry and physiology, it is the aim of this invention to provide a composition of matter which supplies the components required for increasing the intracellular synthesis of ATP.

SUMMARY OF THE INVENTION

The composition of the present invention comprises amino acids, metabolites, electrolytes and a pentose sugar. More specifically, the composition comprises amino acids selected from the group of amino acids which are the metabolic precursors of ATP. The composition further comprises inositol, d-ribose and magnesium phosphate. The composition is formulated so that rapid absorbtion takes place without toxicity due to cell surface alteration.

It has been discovered that when the present invention is administered orally, dramatic increases in intracellular ATP levels and physical performance levels result. Supporting data produced from seven equine case studies demonstrates that post-treatment ATP blood levels, a measure of intracellular ATP levels, increased a remarkable 23.5% on average. Furthermore, in each case a marked improvement occurred in measurable performance parameters and in subjective evaluations.

It has further been discovered that when the present invention is incorporated into a pyrogen-free vehicle and applied locally to a wound site, wound closure rate is increased. The present invention applied as a solution reduces wound size 17.8% faster than controls when applied once daily and 37.2% faster when applied three times daily. A single daily application of gel into which the present invention is incorporated reduces wound size 1.2% faster than control gels, whereas three applications daily reduces wound size 15.7% faster than control gels.

DETAILED DESCRIPTION OF THE INVENTION

1. Increased Intracellular ATP Levels

It has been reported that profound adaptive responses involving alterations in metabolic properties occur in the skeletal muscles of horses undergoing various forms of physical training. Dramatic increases in the concentration of mitochondria and concomitant increases in the concentration of oxidative enzymes involved in ATP production have been frequently documented. In contrast, the anaerobic potential of equine skeletal muscle is intrinsically high and is not greatly influenced by altered patterns of physical activity or nutrition. Accordingly, horses already involved in training programs, provide a particularly appropriate model for evaluating a composition designed to increase intracellular synthesis of ATP.

To establish the efficacy of the present invention, seven Standard-bred horses already involved in training programs were selected. Each of the horses had hematological and blood chemistry studies performed prior to or at the outset of ATP baseline determinations. Blood samples were collected from each subject two to three times a week for a period of twenty-five days while the horses continued to receive their normal training ration of feed. Blood samples were drawn into ACD blood tubes (8.5 ml blood, 1.5 ml anti-coagulent); samples were held on ice until refrigerated at 4° C.

Whole blood was analyzed for levels of ATP within twenty-four hours after bleeding using the Sigma test kit procedure, Sigma Diagnostics, P.O. Box 14508, St. Louis, Mo. 63178. In plasma, ATP is present in trace amounts at best. For this reason, ATP assay procedures require that blood cells be ruptured. Hence, the ATP level found in such an assay is directly related to the intracellular level of ATP. The procedure for ATP determination is based on the action of the enzyme phosphoglycerate phosphatase to form 1, 3 diphosphoglycerate from ATP and 3-phosphoglycerate. The enzyme glyceraldehyde phosphate dehydrogenase catalyzes the reation to form glyceraldehyde-3-P and NAD+P, thus causing a reduction in the absorbance at 340 nm wavelength. The reaction, then, is limited by the amount of ATP present, and the reduction in absorbance is proportional to the ATP present.

After the initial twenty-five day period, four of the subjects received eight ounces daily (4 oz. in A.M. feed, 4 oz. in P.M. feed) of a mixture containing the composition of the present invention and a group of nutritional elements. The remaining three subjects received four ounces daily (2 oz. in A.M. feed,-2 oz. in P.M. feed) of the same mixture. The nutritional elements were combined with the present invention primarily to make it more palatable to the horses and to provide additional vitamins and minerals. The most preferred composition of the present invention is set out in Table I along with the acceptable weight ranges of the individual components. Table II sets out the nutritional elements combined with the present invention in their preferred weight ratios.

TABLE I

| Component | Preferred | Acceptable |
|---|---|---|
| L-glycine | 0.6 Kg | 0.5 Kg–0.7 Kg |
| L-arginine | 2.4 Kg | 2.2 Kg–2.6 Kg |
| D/L methionine | 12.0 Kg | 10.8 Kg–13.2 Kg |
| Choline chloride | 10.1 Kg | 9.1 Kg–11.1 Kg |
| Inositol | 8.9 Kg | 8.0 Kg–9.8 Kg |
| L-aspartic acid | 8.9 Kg | 8.0 Kg–9.8 Kg |
| L-tryptophan | 2.6 Kg | 2.3 Kg–2.9 Kg |
| L-phenylalanine | 2.1 Kg | 1.9 Kg–2.3 Kg |
| L-histidine | 2.0 Kg | 1.8 Kg–2.2 Kg |
| L-proline | 1.5 Kg | 1.4 Kg–1.7 Kg |
| D-ribose | 8.9 Kg | 8.0 Kg–9.8 Kg |
| Magnesium phosphate | 7.7 Kg | 6.9 Kg–8.5 Kg |
| Total | 67.7 Kg | 60.9 Kg–74.6 Kg |

TABLE II

| COMPONENT | |
|---|---|
| Lactalbumin | 300.00 Kg |
| yeast culture *(Saccharomyces cerevisiae)* | 340.90 Kg |
| Dried Beet Molasses | 181.80 Kg |
| Dicalcium phosphate | 90.90 Kg |
| Sodium bicarbonate | 22.70 Kg |
| multi-vitamin mixture (vitamin A, vitamin D3, vitamin E, vitamin B12, riboflavin, niacin, pantothenic acid, menadione, folic acid, thiamine, pyridoxine, ascorbic acid and biotin) | 45.45 Kg |
| Lignan sulphate | 13.07 Kg |
| Flavoring agents | 1.36 Kg |
| Total | 996.18 Kg |

Background information for each horse was collected regarding training performance, stamina, race times and results, and general history. A daily journal was maintained by the trainer for each horse during the study period.

Figure 1:
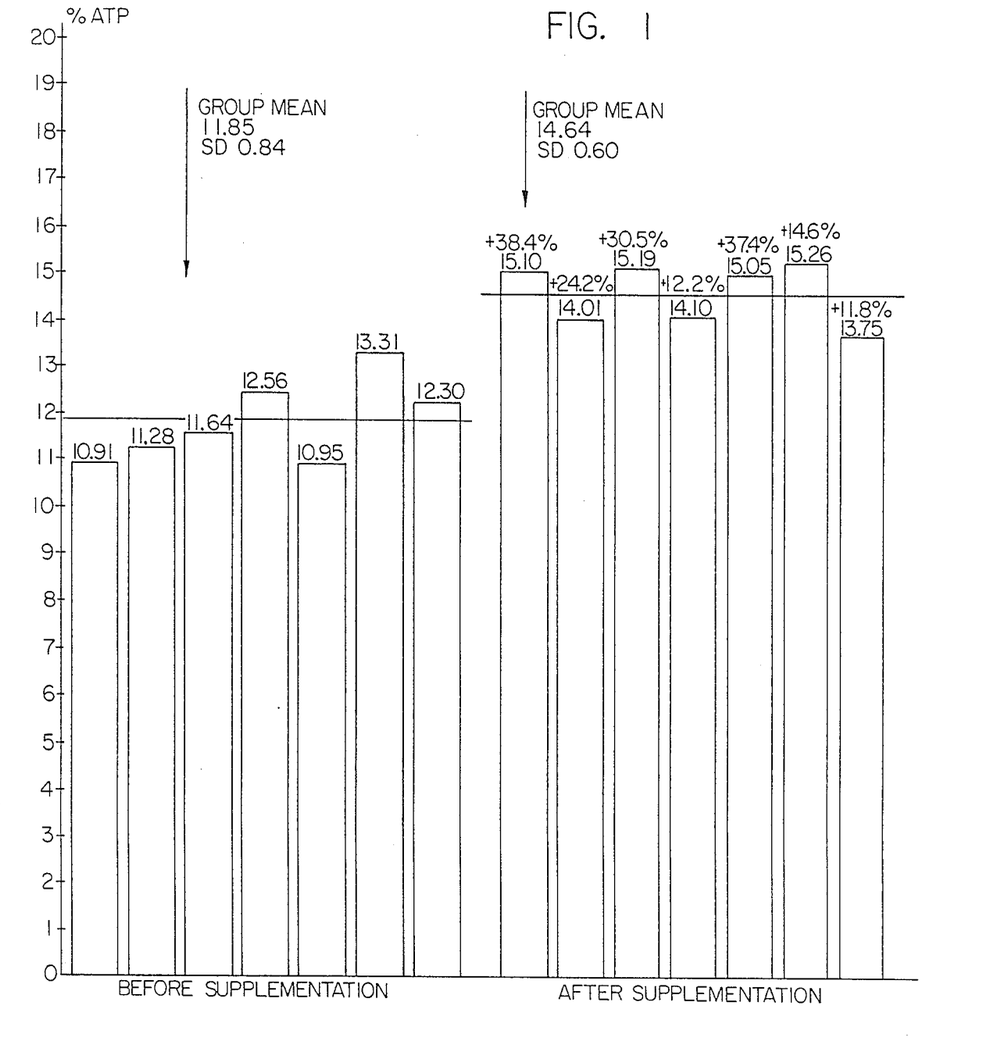
FIG. 1 illustrates ATP blood levels and group mean levels for seven subjects whose diet was supplemented with the present invention.
Figure 2:
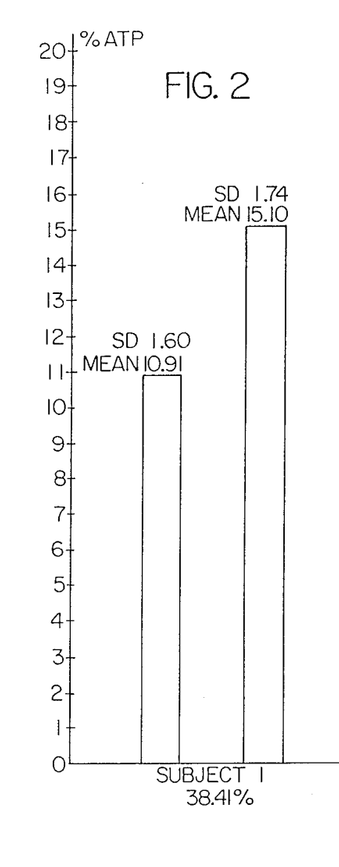
FIGS. 2–8 illustrate mean ATP blood levels for each individual subject before and after dietary supplementation with the present invention.
Figure 3:
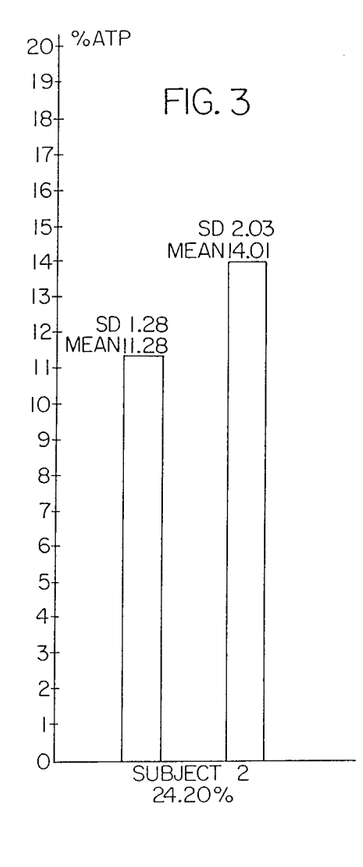
Figure 4:
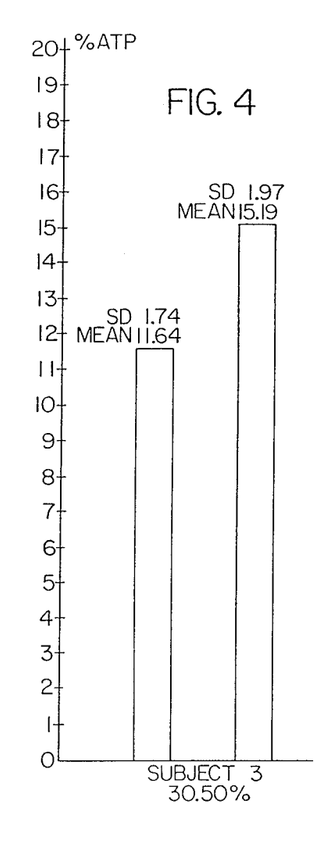
Figure 5:
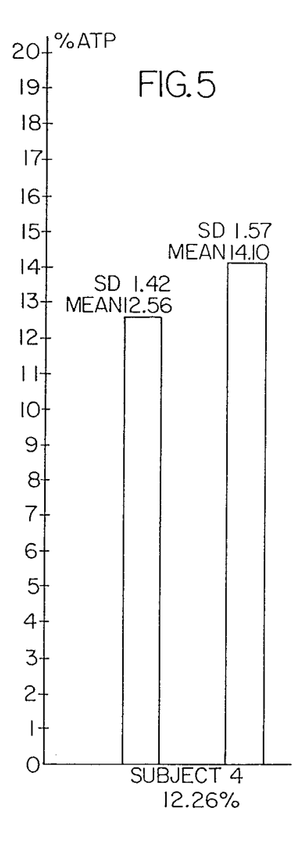
Figure 6:
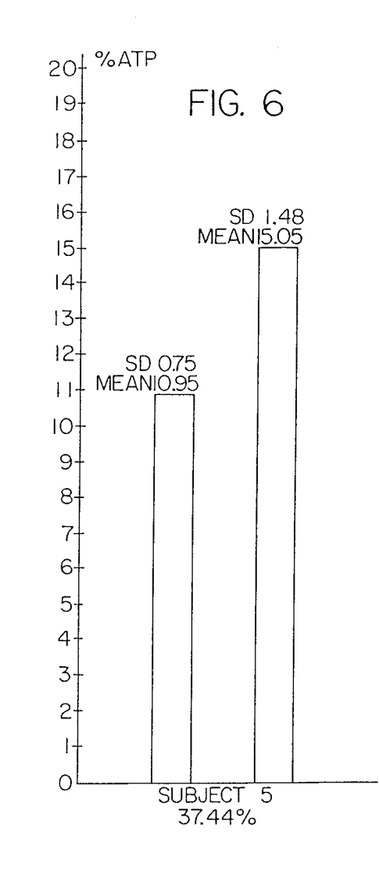
Figure 7:
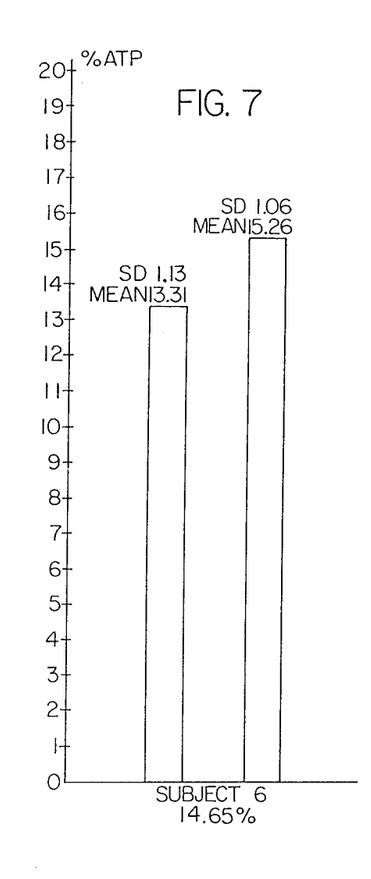
Figure 8:
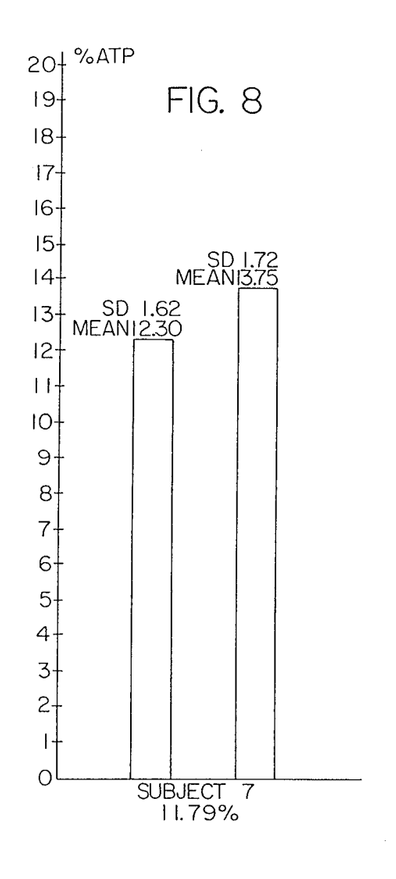
Figure 9:
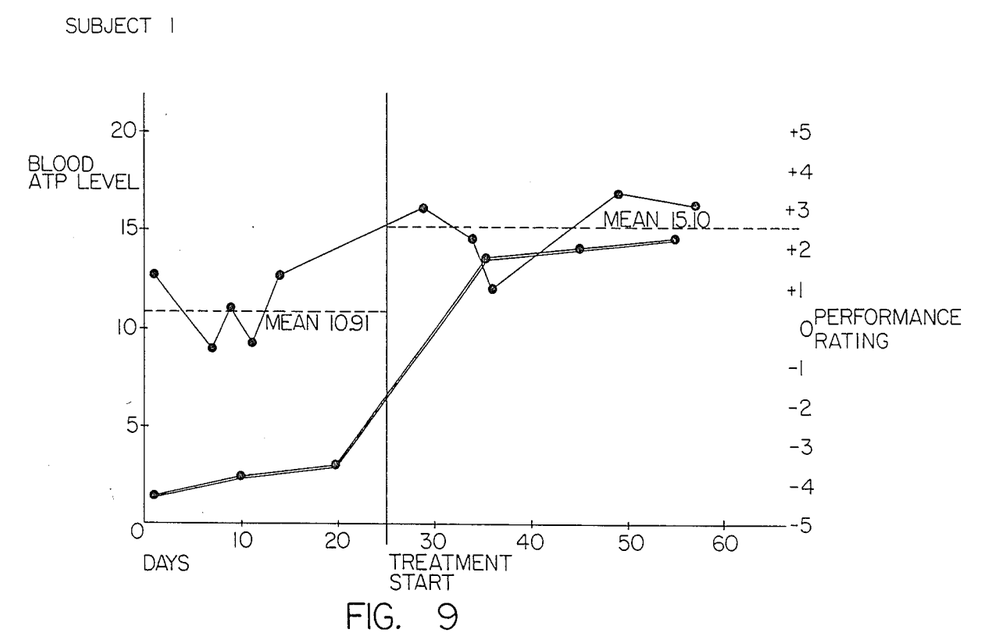
FIGS. 9–12 illustrate the correlation between increased ATP blood levels and increased performance levels for four of the seven subjects.
Figure 10:
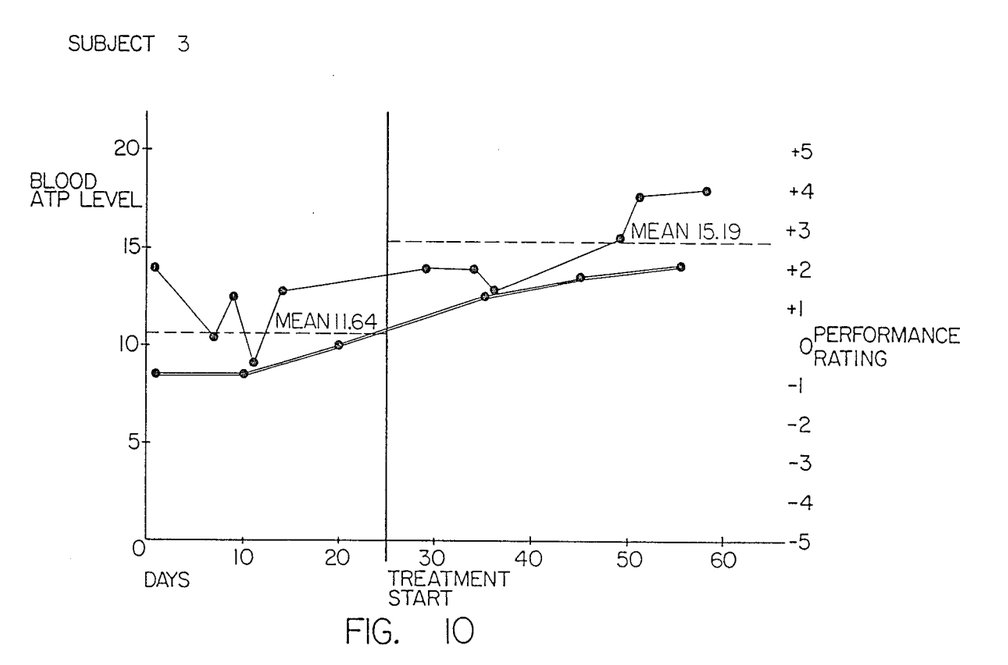
Figure 11:
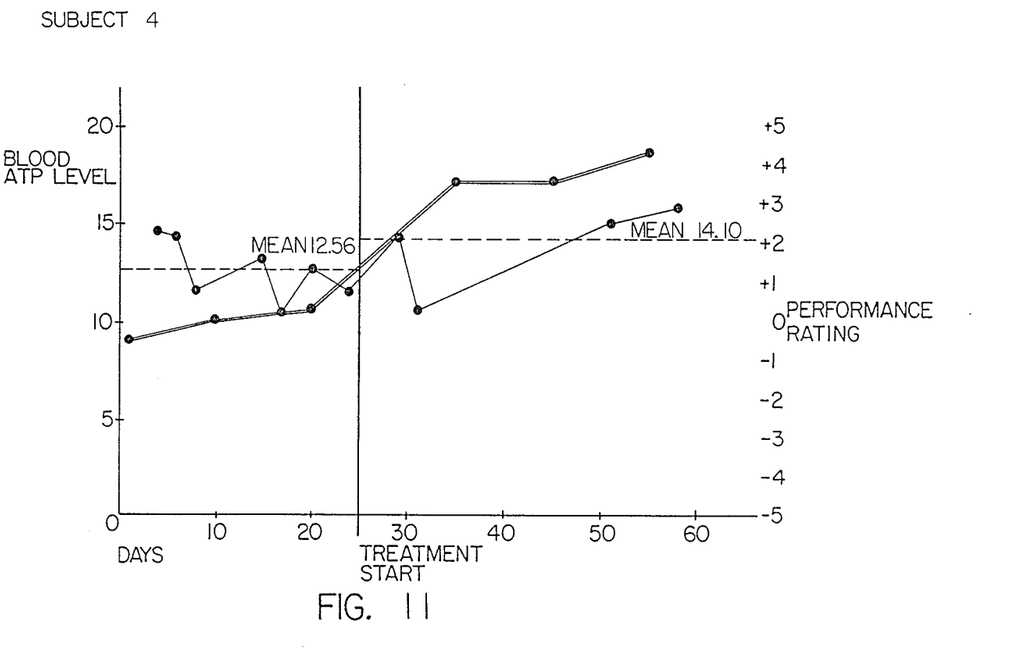
Figure 12:
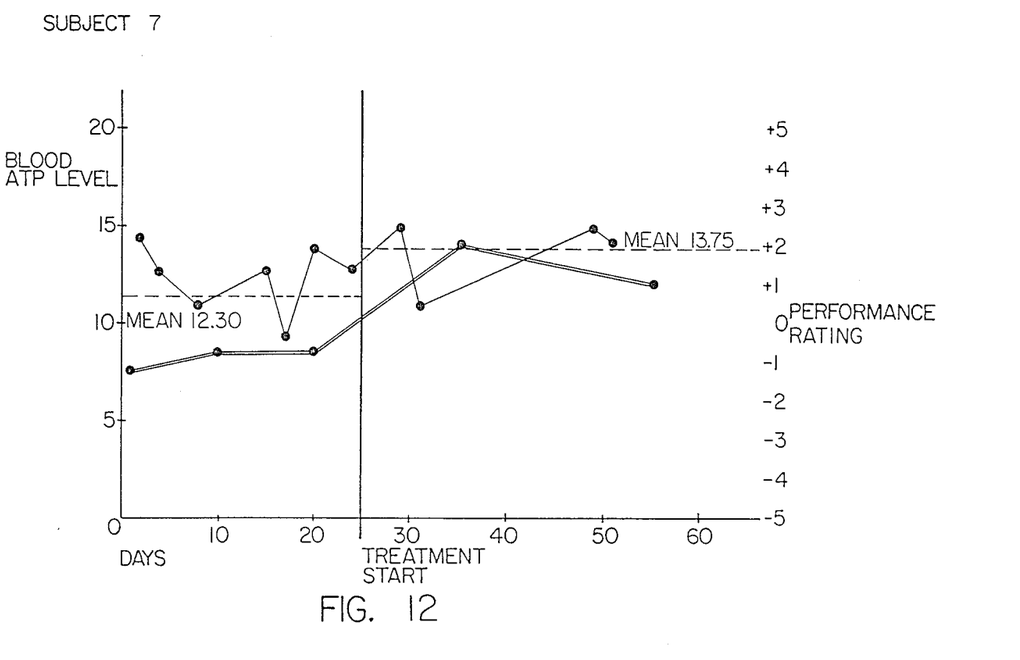

Dietary supplementation with the present invention had a marked effect on the level of ATP in the subjects' blood. As noted above, the blood level of ATP is directly related to the level of ATP inside the cell. FIG. 1 illustrates ATP blood levels for all seven subjects before and after dietary supplementation. As a group, after supplementation, subjects had a mean increase (percentage increase) of ATP blood levels of 23.54%. FIGS. 2–8 illustrate that each individual subject showed marked increase in ATP blood levels ranging from a high of 38.4% (FIG. 2) to a low of 11.8% (FIG. 8).

FIGS. 9–12 illustrate the correlation between increased blood levels of ATP and improved performance levels for four of the seven subjects. FIGS. 9–12 correspond to subjects 1, 3, 4 and 7 respectively. Since these four subjects continue to race competitively and train accordingly, they generated sufficient data to form the basis for an ATP blood level/performance level correlation. The solid line on each of the figures illustrates, in alternate form, the data expressed in the bar graphs of FIGS. 1 ∝ 8. That is, dietary supplementation with the present invention produces a marked increase in ATP blood levels over the levels found in the period immediately preceding the start of supplementation. The broken line on each of FIGS. 9–12 illustrates the mean ATP blood level for the period immediately preceding supplementation and the period of supplementation. The solid double line in each of the FIGS. 9–12 illustrates the correlation between increased blood levels of ATP and increased performance levels.

As noted above, background information for each subject was collected regarding training performance, stamina, race times and results, and general history. The background information was compiled over a period of approximately one year, the period coinciding with the racing season completed prior to the initiation of dietary supplementation with the present invention. The background information consists of quantitative data such as race times, split times and race results. In addition, the background information includes subjective evaluations of the horses by their trainers. The background information collected on each subject was used to establish an average expected behavior or zero rating for each horse. The zero rating was established by evaluating each subject on the basis of four criteria: speed, stamina, aggressiveness and vitality. Each subject was given a rating for each of the four criteria based on a scale of −5 to +5. Once the zero rating for each subject was established, the horses were again evaluated according to the four criteria during the twenty-five day period preceding dietary supplementation and for the period of dietary supplementation. The second and third sets of evaluations resulted in a performance rating relative to the previously determined zero rating for each of the periods just mentioned.

As FIGS. 9–12 clearly illustrate, each of the subjects had a performance level very near to or below their zero rating for the twenty-five day period preceding the initiation of supplementation. However, FIGS. 9–12 also clearly indicate that as ATP blood levels increased during the period of dietary supplementation, performance levels increased to the point where, by the end of the supplementation period, each of the subjects had a performance rating well above the subject's zero rating. In fact, two of the subjects, number 4, a four-year-old, and number 7, a seven-year-old, established new lifetime race marks. It is important to note that at no time during the study were trainers informed of any blood test results.

2. Increased Rate of Wound Repair

To demonstrate that the composition of the present invention increases the rate of wound repair, another series of experiments were conducted wherein the composition was applied to excised wounds on the dorsum of laboratory rats. This was performed as follows: male Sprague-Dawley rats (250–300 g, Charles River Breeding Laboratories, Willmington, Me.) were anesthetized with an intraperitoneal injection of Ketamine/Rompun (90 mg/Ketamine and 10 mg/Rompun). Each rat was given a single full-thickness excized wound 2.5 cm in diameter over the dorsal midline. While the rats were anesthetized, photographs were taken to represent zero time (initial size [area]) compared to a second photograph taken ten days later. For forty-eight hours post-surgery, all animals were maintained on analgesic levels of Acepromazine (0.015%) in their water supply, which eliminated signs of discomfort from the wounds. After the experimental period, the rat were euthanized and skin sections prepared for sub-stage illumination and photographic measurement of final wound area. At this time, the wounded areas were dissected free from surrounding tissue, weighed and frozen in dry ice/acetone for future ATP determination. The process required 45 seconds from the removal of the skin section to freezing in a weighing boat for ATP analysis. The procedures used for ATP determination were the same as those outlined above using the Sigma Diagnostic test kit.

The experimental design consisted of eight (8) groups containing six (6) rats each with treatment summarized as follows:

Group 1—composition of the present invention (1% composition in sterile isotonic saline). The most preferred composition is set out in Table III along with the acceptable weight ranges of the individual components.

Group 2—ATP solution (33 mg per ml in sterile isotonic saline).

Group 3—a solution containing both the composition and ATP combined to give the same concentrations above.

Group 4—the composition in a gel (10% Avalon gel containing 1% of the compostion).

Group 5—ATP in a gel (10% Avalon gel containing 33 mg per ml added in sterile saline).

Group 6—the composition and ATP combined in 10% Avalon gel to provide the same concentrations as above.

Group 7—sterile isotonic saline in a gel.

Group 8—sterile isotonic saline solution.

TABLE III

Composition of ATP-E

| Component | Preferred Grams | Acceptable Grams |
|---|---|---|
| L - glycine | 8.9 | 8.0–9.8 |
| L - arginine | 35.4 | 31.9–38.9 |
| D/L methionine | 177.2 | 159.5–194.9 |
| Choline chloride | 149.2 | 134.3–164.1 |
| Inositol | 131.5 | 118.3–144.7 |
| L - aspartic acid | 131.5 | 118.3–144.7 |
| L - tryptophan | 38.4 | 34.6–42.2 |
| L - phenylalanine | 31.0 | 27.9–34.1 |
| L - histidine | 29.5 | 26.5–32.4 |
| L - proline | 22.2 | 20.0–24.4 |
| D - ribose | 131.5 | 118.4–144.7 |
| Magnesium phosphate | 113.7 | 102.3–125.1 |
| | 1000.0 | 900.0–1100.0 |

Treatments with the above solutions and gels were administered once daily in the first trial reported here. In the second trial, solutions and gels were applied three times daily for the first three days, then once daily for seven days. Each application consisted of either 0.5 ml of solution or 0.5 g of gel. At the end of the ten day period in both trials, the rats were euthanized and wound tissues taken for study.

The procedure for wound size measurements was as follows: Wound size measurements were made from standardized photographs, and area was determined with a planimeter. The sections were photgraphed with standardized magnification, and planimetric measurement was made of the wound outline. A metric scale in the plane of the wound assured reproducable determinations.

Figure 13:
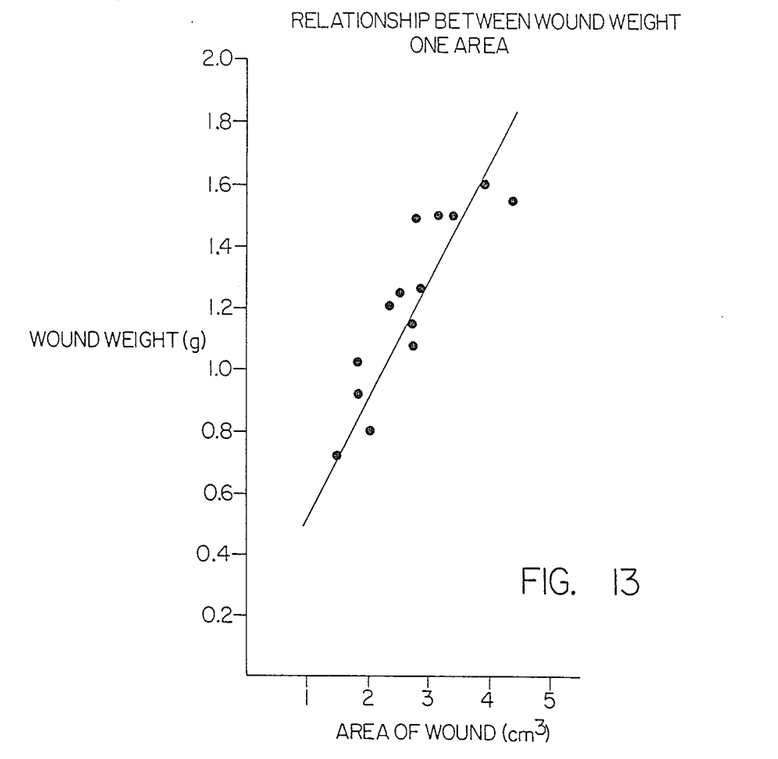
FIG. 13 illustrates the relationship between wound surface area and wound weight in a series of experiments conducted wherein the present invention was applied to excised wounds on the dorsum of laboratory rats.

Wound weights were determined by making an excision of the entire wound down to the panus. FIG. 13 shows the correlation between wound area surface and wound weight, thus providing a basis for determinations on either weight or area.

After each wound was removed it was immediately frozen at $-80°$ C. for wound weight and ATP determinations. The concentration of ATP was determined in wound tissue by mincing the entire section containing granulation tissue. The ATP levels were expressed as ATP milligram/10 g of tissue.

The data set out in Table IV below demonstrates that a single daily application of the composition as a solution produced a rate of closure which was 17.8% faster than wounds treated with sterile isotonic saline (control). When the composition was applied as a gel, the rate was 1.2% faster. The composition applied three times a day as a solution produced a marked improvement over treatments applied once each day. The data shown in Table V demonstrates these improvements, wherein composition treated wounds had a mean reduction of 37.1%, ATP 31.2% and the mixture composition/ATP 37.3%. The values for percent reduction are based on a decrease in wound weight compared to the mean wound weight of 1.153 for the isotonic saline treated control wounds.

TABLE IV

Percent Increase in Contraction Rate Over Control When Applied Once Each Day for 10 Days

| Group | Initial | Final | Difference | % Increase Over Control* |
|---|---|---|---|---|
| I | Composition Soln. 136.6(+7.30) | 59.3(+12.3) | 77.3 | 17.8 |
| II | ATP Soln. 130.5(+12.8) | 61.1(+94) | 69.4 | 5.8 |
| III | Composition Gel 127.9(+6.7) | 61.5(+13.2) | 66.4 | 1.2 |
| IV | ATP Gel 133.5(+5.8) | 71.9(+7.4) | 61.6 | (6) |
| V | Saline Gel Control 135.6(+5.5) | 64.3(+11.5) | 71.3 | — |
| VI | Isotonic Saline Conrol | 72.3(+14.4) | 65.6 | — |

*Value for difference (initial minus final) for treated minus that difference for control divided by control times 100 equals percent increase in contraction rate.

TABLE V

Percent Reduction in Wound Weight

| | Wound Weight | Percent Reduction* |
|---|---|---|
| Group I COMPOSITION | | |
| 1 | — | — |
| 2 | 0.832 | 27.9 |
| 3 | — | — |
| 4 | 0.627 | 45.6 |
| 5 | 0.706 | 38.7 |
| 6 | 0.736 | 36.2 |
| Group II ATP | | |
| 1 | 0.765 | 33.7 |
| 2 | 0.855 | 25.9 |
| 3 | 1.053 | 8.7 |
| 4 | 0.614 | 46.8 |
| 5 | 0.838 | 27.4 |
| 6 | 0.642 | 44.4 |

For Group I COMPOSITION: 37.1 ± 7.3
For Group II ATP: 31.2 ± 13.9

TABLE V-continued

Percent Reduction in Wound Weight

| | Wound Weight | Percent Reduction* | |
|---|---|---|---|
| Group III MIXTURE COMPOSITION/ATP | | | |
| 1 | 0.887 | 23.1 | |
| 2 | 0.708 | 38.6 | |
| 3 | 0.700 | 39.3 | 37.3 ± 8.2 |
| 4 | 0.734 | 36.4 | |
| 5 | 0.589 | 48.9 | |
| 6 | 0.721 | 37.5 | |
| Group VIII Isosaline Control, Valued used for above calculations calculations was 1.153 ± 0.131 | | | |
| 1 | 1.270 | | |
| 2 | 1.131 | | |
| 3 | 0.976 | | |
| 4 | 1.234 | | |
| 5 | 1.026 | | |
| 6 | 1.284 | | |

*The control value minus treated value and that difference divided by the control times 100 yields percent reduction.

Figure 14:
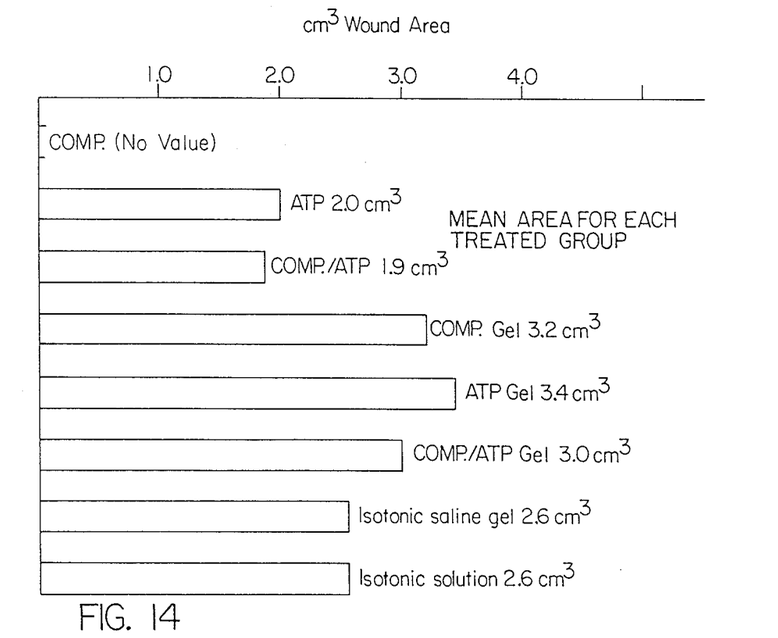
FIG. 14 illustrates the increased rate of wound contraction produced by gels containing the present invention and ATP as compared to a control gel.

FIG. 13 shows the relationship between wound surface area and wound weight. The linear relationship between weight and area suggests that weight measurements may be a useful means for determining wound contraction. The bar graph shown in Fig. 14 depicts the increased rate of contraction for composition/ATP mixture gels compared to control gels. Although the gel treated wounds contracted faster than controls, they did not contract as fast as the solution treated wounds. However, in each group wounds treated with the composition or the composition/ATP mixture had greater rates of contraction than their counterparts.

Figure 15:
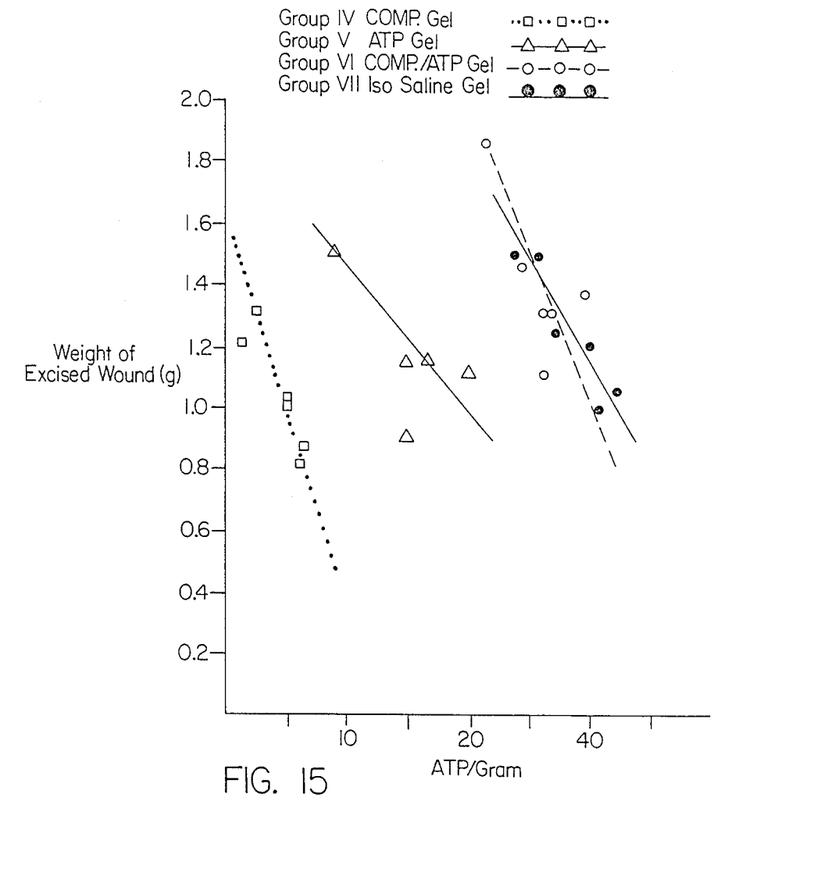
FIGS. 15 and 16 illustrate the relationship between the reduction in wound weight and the amount of ATP found in the wound for gel-treated wounds.
Figure 16:
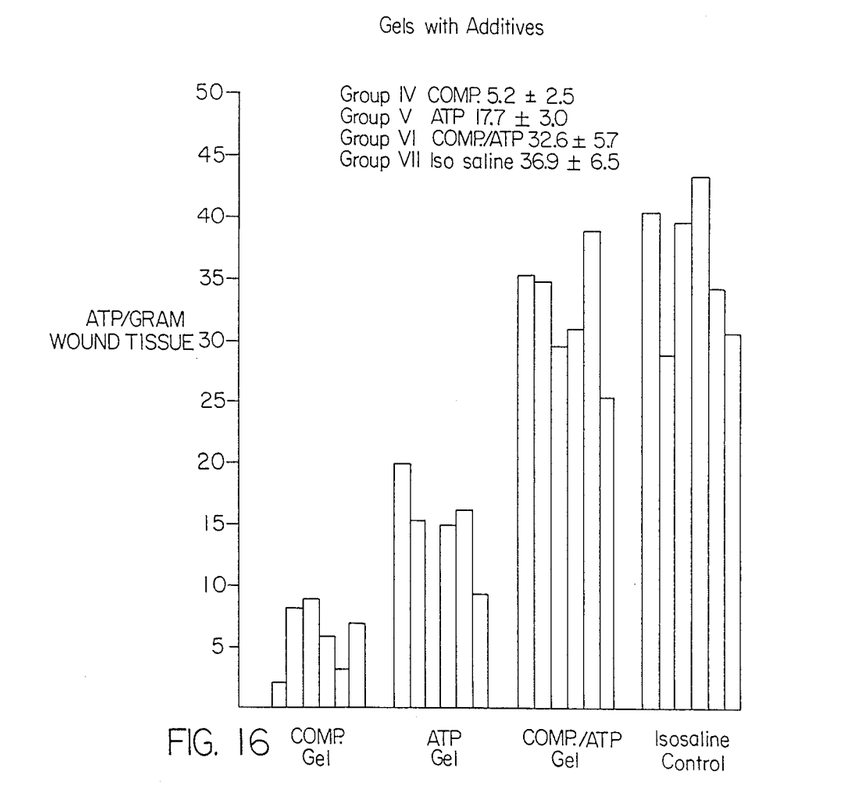

Both solution and gel treatments, in addition to producing a marked reduction in wound weight, also reduced the amount of ATP found in the wound. This is evident in Tables VI and VII and in FIGS. 15 and 16. While it is apparent both in gel and solution treated wounds that ATP levels are reduced by the composition, the reduced level of ATP at the wound site is not unexpected, since protein metabolism for wound repair and the wound contraction produced by the myofibroblasts both require significant amounts of energy in the form of ATP. That is, additional intracellular ATP synthesized by the cells in response to the present invention is quickly utilized for contraction, glueoneogenisis and protein synthesis.

TABLE VI

Solutions Applied to Excised Wounds

| | Wound Wt. | Initial OD | Final OD | ATP | ATP/G | Mean |
|---|---|---|---|---|---|---|
| Group I | | | | | | |
| 1 | 0 | — | — | — | — | |
| 2 | 0.832 | 0.645 | 0.616 | 7.4 | 8.89 | ATP |
| 3 | 1.668 | 0.654 | 0.638 | 6.2 | 3.72 | 8.78 ± 2.57 |
| 4 | 0.627 | 0.654 | 0.631 | 8.0 | 12.8 | Tissue Wt. |
| 5 | 0.706 | 0.671 | 0.638 | 12.9 | 18.3 | 0.725 ± .08 |
| 6 | 0.736 | 0.639 | 0.615 | 9.4 | 12.8 | |
| Group II | | | | | | |
| 1 | 0.765 | 0.454 | 0.420 | 13.3 | 17.4 | |
| 2 | 0.855 | 0.454 | 0.451 | 1.2 | 1.40 | ATP |
| 3 | 1.053 | 0.454 | 0.468 | — | | 8.9 ± 5.37 |
| 4 | 0.614 | 0.418 | 0.427 | — | | Tissue Wt. |
| 5 | 0.838 | 0.418 | 0.450 | 11.7 | 14.0 | 0.794 ± .160 |
| 6 | 0.642 | 0.469 | 0.450 | 7.4 | 14.6 | |
| Group III | | | | | | |
| 1 | 0.887 | 0.631 | 0.591 | 15.6 | 17.6 | |
| 2 | 0.708 | 0.445 | 0.485 | — | | ATP |
| 3 | 0.700 | 0.423 | 0.436 | — | | 6.9 ± 6.18 |

TABLE VI-continued

Solutions Applied to Excised Wounds

| | Wound Wt. | Initial OD | Final OD | ATP | ATP/G | Mean |
|---|---|---|---|---|---|---|
| 4 | 0.734 | 0.423 | 0.417 | 2.3 | 3.1* | Tissue Wt. |
| 5 | 0.589 | 0.423 | 0.405 | 7.0 | 11.9 | 0.723 ± .095 |
| 6 | 0.721 | 0.609 | 0.602 | 2.7 | 3.7 | |
| Group VIII | | | | | | |
| 1 | 1.270 | 0.515 | 0.500 | 5.9 | 4.7 | |
| 2 | 1.131 | 0.474 | 0.468 | 2.3 | 2.0 | ATP |
| 3 | 0.976 | 0.495 | 0.478 | 6.6 | 6.8 | 7.64 ± 4.75 |
| 4 | 1.234 | 0.477 | 0.478 | — | | Tissue Wt. |
| 5 | 1.026 | 0.477 | 0.456 | 8.2 | 8.0 | 1.153 ± 0.131 |
| 6 | 1.284 | 0.670 | 0.631 | 15.2 | 11.8 | |

TABLE VII

Gels Applied to Excised Rat Wounds
(Three Applications Per Day)

| | Wound Wt. | Initial OD | Final OD | ATP | ATP/G | Mean |
|---|---|---|---|---|---|---|
| Group IV Composition Gel | | | | | | |
| 1 | 1.218 | 0.553 | 0.549 | 1.6 | 1.3 | |
| 2 | 0.805 | 0.579 | 0.565 | 5.5 | 6.8 | ATP |
| 3 | 0.882 | 0.565 | 0.548 | 6.6 | 7.5 | 5.2 ± 2.5 |
| 4 | 1.139 | 0.565 | 0.548 | 6.6 | 5.8 | Tissue Wt. |
| 5 | 1.376 | 0.580 | 0.570 | 3.9 | 2.8 | 1.082 ± 0.212 |
| 6 | 1.076 | 0.956 | 0.938 | 7.2 | 6.7 | |
| Group V | | | | | | |
| 1 | 1.100 | 0.774 | 0.717 | 22.2 | 20.2 | |
| 2 | .954 | 0.815 | 0.777 | 14.8 | 15.5 | ATP |
| 3 | 1.236 | 0.906 | 0.588 | 124.0 | 100.3 | 17.7 ± 3.0 |
| 4 | 1.158 | 0.749 | 0.704 | 17.6 | 15.2 | Tissue Wt. |
| 5 | 1.157 | 0.929 | 0.881 | 18.7 | 16.2 | 1.196 ± 0.207 |
| 6 | 1.574 | 0.608 | 0.569 | 15.2 | 9.7 | |
| Group VI Mixture Composition/ATP Gel | | | | | | |
| 1 | 1.336 | 0.580 | 0.458 | 47.6 | 35.6 | |
| 2 | 1.111 | 0.598 | 0.498 | 39.0 | 35.1 | ATP |
| 3 | 1.480 | 0.592 | 0.479 | 44.1 | 29.8 | 32.6 ± 5.7 |
| 4 | 1.338 | 0.678 | 0.568 | 42.9 | 32.1 | Tissue Wt. |
| 5 | 1.390 | 0.595 | 0.453 | 55.4 | 39.9 | 1.425 ± 0.260 |
| 6 | 1.896 | 0.595 | 0.482 | 44.1 | 23.3 | |
| Group VII Isosaline Gel Control | | | | | | |
| 1 | 1.073 | 0.635 | 0.520 | 44.9 | 41.8 | |
| 2 | 1.540 | 0.628 | 0.520 | 42.1 | 27.3 | ATP |
| 3 | 1.219 | 0.604 | 0.476 | 49.9 | 40.9 | 36.9 ± 6.5 |
| 4 | 1.127 | 0.604 | 0.476 | 49.9 | 44.3 | Tissue Wt. |
| 5 | 1.256 | 0.577 | 0.465 | 43.7 | 34.8 | 1.285 ± 0.192 |
| 6 | 1.496 | 0.617 | 0.494 | 48.0 | 32.1 | |

In summary, solutions and gels containing the composition of the present invention caused an improvement in wound closure rate over that of controls consisting of sterile isotonic saline. The wound repair rate appeared dose dependent in reference to the number of applications made; that is, one application daily produced a 17.8% faster rate of wound closure and three applications per day produced a 37.2% faster rate. As in any other bioassay, dose related responses are significant from the standpoint of data validity. Composition containing solutions and gels caused an improved wound closure rate over that of controls by increasing the available components for gluconeogenesis and protein synthesis. In addition, increased intracellular ATP synthesized by the cells in response to the present invention was quickly utilized as an energy source for these processes and for the wound contraction mechanism. Finally, the stoichiometry of wound weight to wound size was consistent as was the inverse relationship between wound weight and ATP levels.

I claim:

1. A composition of matter for increasing the intracellular level of ATP comprising:
   amino acids selected from the group of amino acids which are the metabolic precursors of ATP;
   at least one metabolite selected from the group consisting of choline chloride and inositol;
   electrolyte; and
   ribose.

2. The composition of claim 1 wherein the amino acids consist of L-glycine, L-arginine, D/L methionine, L-aspartic acid, L-tryptophan, L-pheylalanine, L-histidine and L-proline.

3. The composition of claim 1 wherein the metabolites consist of choline chloride and inositol.

4. The composition of claim 1 wherein the electrolyte consists of magnesium phosphate.

5. The composition of claim 1 consisting of by weight percentage: L-glycine (0.80–98%), L-arginine (3.19–3.89%), D/L-methionine (15.95–19.49%), choline chloride (13.43–16.41%), inositol (11.83–14.47%), L-aspartic acid (11.83–14.47%), L-tryptophan (3.46–4.22%), L-pheylalanine (2.79–3.41%), L-histidine (2.65–3.24%), L-proline (2.00–2.44%), D-ribose (11.84–14.47%) and magnesium phosphate (10.23–12.51%).

6. A composition of matter for increasing the intracellular synthesis of ATP consisting of by weight percentage: L-glycine (0.89%), L-arginine (3.54%), D/L methionine (17.72%), choline chloride (14.92%), inositol (13.15%), L-aspartic acid (13.15%), L-tryptophan (3.84%), L-pheylalanine (3.10%), L-histidine (2.95%), L-proline (2.22%), D-ribose (13.15%) and magnesium phosphate (11.37%).

7. A mixture for increasing the intracellular level of ATP and physical performance levels in horses comprising: amino acids selected from the group of amino acids which are the metabolitic precursors of ATP; at least one metabolite selected from the group consisting of choline chloride and inositol; electrolyte, ribose, vitamins, minerals and flavoring agents.

8. The mixture of claim 7 wherein the amino acids consist of L-glycine, L-arginine, D/L methionine, L-aspartic acid, L-tryptophan, L-pheylalanine, L-histidine and L-proline.

9. The mixture of claim 7 wherein the metabolites consist of choline chloride and inositol.

10. The mixture of claim 7 wherein the electrolyte consist of magnesium phosphate.

11. The mixture of claim 7 consisting of by weight; L-glycine (0.6 Kg), L-arginine (2.4 Kg), D/L methionine (12.0 Kg), choline chloride (10.1 Kg), inositol (8.9 Kg), L-aspartic acid (8.9 Kg), L-tryptophan (2.6 Kg), L-pheylalanine (2.1 Kg), L-histidine (2.0 Kg), L-proline (1.5 Kg), ribose (8.9 Kg), magnesium phosphate (7.7 Kg), lactalbumin (300 Kg), *Saccharomyces cerevisiae* culture (340.9 Kg), dried beet molasses (181.8 Kg), dicalcium phosphate (90.9 Kg), sodium bicarbonate (22.7 Kg), a multi-vitamin mixture comprising vitamin A, vitamin D3, vitamin E, vitamin B12, riboflavin, niacin, pantothenic acid, menadione, folic acid, thiamine, pyridoxine, ascorbic acid and biotin (45.45 Kg), lignan sulphate (13.07 Kg) and flavoring agents (1.36 Kg).

12. A pharmaceutical preparation for increasing the rate of wound repair consisting of by weight percentage: L-glycine (0.80–0.98%), L-arginine (3.19–3.89%), D/L methionine (15.95–19.49%), choline chloride (13.43–16.41%), inositol (11.83–14.47%), L-aspartic acid (11.83–14.47%), L-tryptophan (3.46–4.22%), L-pheylalanine (2.79–3.41%), L-histidine (2.65–3.24%), L-proline (2.0–2.44%), D-ribose (11.84–14.47%) and magnesium phosphate (10.23–12.51%).

13. A pharmaceutical preparation for increasing the rate of wound repair consisting of by weight percentage: L-glycine (0.89%), L-arginine (3.54%), D/L methionine (17.72%), choline chloride (14.92%), inositol (13.15%), L-aspartic acid (13.15%), L-tryptophan (3.84%), L-pheylalanine (3.1%), L-histidine (2.95%), L-proline (2.22%), D-ribose (13.15%) and magnesium phosphate (11.37%).

14. The preparation of claim 13 wherein the preparation is solubilized in normal saline.

15. The preparation of claim 13 wherein the preparation is solubilized in normal saline at a 1% w/v concentration.

16. The preparation of claim 13 wherein the preparation is incorporated into a gel.

17. The preparation of claim 13 wherein the preparation is incorporated into the gel at a 1% w/v concentration.

* * * * *